US006482436B1

(12) United States Patent
Volkonsky et al.

(10) Patent No.: US 6,482,436 B1
(45) Date of Patent: *Nov. 19, 2002

(54) MAGNETICALLY RESPONSIVE COMPOSITION

(75) Inventors: Viktor A. Volkonsky; Sergei D. Dyuksherstnov; Sergi V. Chernyakov, all of Mosow (RU); Larry M. Allen, Golden; Thomas B. Kent, Boulder, both of CO (US)

(73) Assignee: FeRx Incorporated, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/226,818

(22) Filed: Jan. 6, 1999

(Under 37 CFR 1.47)

Related U.S. Application Data

(63) Continuation-in-part of application No. 09/003,286, filed on Jan. 6, 1998, which is a continuation-in-part of application No. 08/480,195, filed on Jun. 7, 1995, now Pat. No. 5,705,195, which is a continuation of application No. 08/188,062, filed on Jan. 26, 1994, now Pat. No. 5,549,915, which is a continuation-in-part of application No. 08/011,363, filed on Jan. 29, 1993, now abandoned.

(51) Int. Cl.[7] .............................. A61K 9/14; A61K 9/16; A61K 13/00; A61K 13/02
(52) U.S. Cl. ....................... 424/489; 424/490; 424/443; 424/448; 424/445; 424/447
(58) Field of Search ................................ 424/489, 490, 424/443, 448, 445, 447

(56) References Cited

U.S. PATENT DOCUMENTS

| | | | |
|---|---|---|---|
| 3,717,594 A | 2/1973 | Miller | 252/62.1 |
| 4,106,488 A | 8/1978 | Gordon | 424/85 |
| 4,247,406 A | 1/1981 | Widder et al. | 252/62.53 |
| 4,331,654 A | 5/1982 | Morris | 252/62.1 |
| 4,345,588 A | 8/1982 | Widder et al. | 128/260 |
| 4,501,726 A | 2/1985 | Schroder et al. | 604/890 |
| 4,652,257 A | 3/1987 | Chang | 604/52 |
| 4,690,130 A | 9/1987 | Mirell | 424/85 |
| 4,818,614 A | 4/1989 | Fukui et al. | 428/403 |
| 4,849,209 A | 7/1989 | Lieberman et al. | 534/10 |
| 4,871,716 A | 10/1989 | Longo et al. | 424/491 |
| 4,963,360 A * | 10/1990 | Argaud | 424/443 |
| 5,549,915 A | 8/1996 | Volkonsky et al. | 424/490 |
| 5,651,989 A | 7/1997 | Volkonsky et al. | 424/490 |
| 5,705,195 A | 1/1998 | Volkonsky et al. | 424/490 |
| 5,776,925 A | 7/1998 | Young et al. | 514/185 |
| 5,827,533 A | 10/1998 | Needham | 424/450 |
| 6,200,547 B1 * | 3/2001 | Volkonsky et al. | |

FOREIGN PATENT DOCUMENTS

EP 0451299 10/1995
WO WO 91/06322 5/1991

OTHER PUBLICATIONS

Imshennik et al., "The formation of magnetic iron cluster on activated carbon", Chemical Abstracts Service, Columbus, Ohio; Hyperfine Interact, 57 (1–4), 1875–81, 1990; Hyindn: ISSN: 0304–03843, 1990.
Patent Abstracts of Japan, vol. 008, No. 241 (C–250), Nov. 6, 1984; and JP A–59 122429, Jul. 14, 1984.
Allen et al., "A Magnetically Targetable Drug Carrier for Paclitaxel", Scientific and Clinical Applications of Magnetic Carriers, New York, 1997, pp. 481–494.

* cited by examiner

*Primary Examiner*—Thurman K. Page
*Assistant Examiner*—Amy E Pulliam
(74) *Attorney, Agent, or Firm*—Fish & Richardson P.C.

(57) ABSTRACT

A magnetically controllable, or guided, ferrocarbon particle composition and methods of use and production are disclosed. The composition may optionally carry biologically active substances that have been adsorbed onto the particle. The composition comprises composite, volume-compounded particles of 0.1 to 5.0 μm in size, and preferably between 0.5 and 5.0 μm, containing 1.0 to 95.0% by mass of carbon, and preferably from about 20% to about 60%. The particles may be produced by mechanical milling of a mixture of iron and carbon powders. The obtained particles are optionally placed in a solution of a biologically active substance to adsorb the substance onto the particles. The composition is generally administered in suspension.

74 Claims, 5 Drawing Sheets

MAGNETICALLY RESPONSIVE COMPOSITION

RELATED APPLICATION

This is a continuation-in-part of U.S. application Ser. No. 09/003,286, filed Jan. 6, 1998, (pending), which is a continuation-in-part-of U.S. patent application Ser. No. 08/480,195, filed Jun. 7, 1995 (now U.S. Pat. No. 5,705,195), which is a continuation of U.S. application Ser. No. 08/188,062, filed Jan. 26, 1994 (now U.S. Pat. No. 5,549,915), which is a continuation-in-part of U.S. patent application Ser. No. 08/011,363, filed Jan. 29, 1993 now abandoned.

FIELD OF INVENTION

This invention relates to compositions and methods for delivery of biocompatible particles to a selected location in a body, and, more particularly, relates to particles capable of carrying biologically active compounds, which provide for targeted magnetic transport of the particles and the maintenance of them in a predetermined place for localized diagnostic or therapeutic treatment of disease.

BACKGROUND OF THE INVENTION

Metallic carrier compositions used in the treatment of various disorders have been heretofore suggested and/or utilized (see, for example, U.S. Pat. Nos. 4,849,209 and 4,106,488), and have included such compositions that are guided or controlled in a body in response to external application of a magnetic field (see, for example, U.S. Pat. Nos. 4,501,726, 4,652,257 and 4,690,130). Such compositions have not always proven practical and/or entirely effective. For example, such compositions may lack adequate capacity for carriage of the desired biologically active agent to the treatment site, have less than desirable magnetic susceptibility and/or be difficult to manufacture, store and/or use.

One such known composition, deliverable by way of intravascular injection, includes microspheres made up of a ferromagnetic component covered with a biocompatible polymer (albumin, gelatin, and polysaccharides) which also contains a drug (Driscol C. F. et al. *Prog. Am. Assoc. Cancer Res.*, 1980, p. 261).

It is possible to produce albumen microspheres up to 3.0 $\mu$m in size containing a magnetic material (magnetite $Fe_3O_4$) and the anti-tumoral antibiotic doxorubicin (Widder K. et al. *J. Pharm. Sci.*, 68:79–82 1979). Such microspheres are produced through thermal and/or chemical denaturation of albumin in an emulsion (water in oil), with the input phase containing a magnetite suspension in a medicinal solution. Similar technique has been used to produce magnetically controlled, or guided, microcapsules covered with ethylcellulose containing the antibiotic mitomycin-C (Fujimoto S. et al., *Cancer*, 56: 2404–2410,1985).

Another method is to produce magnetically controlled liposomes 200 nm to 800 nm in size carrying preparations that can dissolve atherosclerotic formations. This method is based on the ability of phospholipids to create closed membrane structures in the presence of water (Gregoriadis G., Ryman B. E., *Biochem. J.*, 124:58, 1971).

The above compositions require extremely high flux density magnetic fields for their control, and are somewhat difficult to produce consistently, sterilize, and store on an industrial scale without changing their designated properties.

To overcome these shortcomings, a method for producing magnetically controlled dispersion has been suggested (See European Patent Office Publication No. 0 451 299 A1, by Kholodov L. E., Volkonsky V. A., Kolesnik N. F. et al.), using ferrocarbon particles as a ferromagnetic material. The ferrocarbon particles are produced by heating iron powder made up of particles 100 $\mu$m to 500 $\mu$m in size at temperatures of 800° C. to 1200° C. in an oxygen-containing atmosphere. The mixture is subsequently treated by carbon monoxide at 400° C. to 700° C. until carbon particles in an amount of about 10% to 90% by mass begin emerging on the surface. A biologically active substance is then adsorbed on the particles This method of manufacturing ferrocarbon particles is rather complicated and requires a considerable amount of energy. Because the ferromagnetic component is oxidized due to the synthesis of ferrocarbon particles at a high temperature in an oxygen containing atmosphere, magnetic susceptibility of the dispersion obtained is decreased by about one-half on the average, as compared with metallic iron. The typical upper limit of adsorption of a biologically active substance on such particles is about 2.0% to 2.5% of the mass of a ferromagnetic particle.

The magnetically controlled particle produced by the above method has a spherical ferromagnetic component with a thread-like carbon chain extending from it and is generally about 2.0 $\mu$m in size. The structure is believed to predetermine the relatively low adsorption capacity of the composites and also leads to breaking of the fragile thread-like chains of carbon from the ferromagnetic component during storage and transportation.

Thus, there remains a need for an effective biocompatible composition which is capable of being transported magnetically, and which is relatively easy to manufacture, store and use.

SUMMARY OF THE INVENTION

This invention provides a magnetically responsive composition which may carry biologically active substances, or which may be used alone. Generally, any soluted substance can be carried, many of which have been heretofore suggested. For example, without limitation, alkylating agents, antimetabolites, antifungals, anti-inflammatory, antitumor, and chemotherapy agents, and suitable combinations thereof can be adsorbed on the particles. Other therapeutic agents and drugs, such as systemic toxicity inhibitors, antibiotics and hydrocortisone, or the like, can also be carried and administered in vivo by use of the magnetically controlled carrier particles of the invention. Methods of production and use thereof are also provided.

The aim of this invention is to improve some parameters of magnetically controlled compositions used for the targeted transport of biocompatible particles, including increasing relative adsorption capacity, increasing magnetic susceptibility, intensifying diagnostic and therapeutic effect and ease of use, as well as simplifying the technology of manufacturing the magnetically controlled composition and ensuring its guaranteed long storage without changing its desired characteristics.

This is achieved by using suitable composite,volume compounded ferrocarbon particles as a magnetically susceptible material for a magnetically controlled composition. These particles have a major dimension (i.e., largest diameter) of about 0.2 $\mu$m to about 5.0 $\mu$m (and preferably from 0.5 $\mu$m to 5.0 $\mu$m) and contain from about 1.0% to about 95.0% (by mass) of carbon, with the carbon strongly connected to iron. The particles are obtained by jointly deforming (i.e., milling) a mixture of iron and carbon powders. In some cases the finished particles include trace amounts of the compound cementite ($Fe_3C$).

The composition utilized for localized in vivo treatment of disease includes particles of about 0.5 μm and 5 μm in major dimension, each particle including carbon and iron and, optionally, a biologically active substance selected for its efficacy in diagnosing or treating the disease adsorbed on the particles.

The method of producing the composition includes the step of jointly deforming a mechanical mixture of iron and carbon powders for a time sufficient to bind the powders into a composite of iron:carbon particles having an average major dimension of less than 5 μm in size, and with a substantial portion of the particles including about 1.0% to 95.0% by mass of carbon distributed throughout the volume of each of the particles. The particles are preferably separated to select particles having a major dimension of from about 0.5 μm to about 5.0 μm, after which up to 20% by mass of the particles of a biologically active substance can be adsorbed onto the selected particles.

The methods of use include methods for localized in vivo diagnosis or treatment of disease comprising providing a magnetically responsive ferrocarbon carrier (such as the carrier of this invention) having adsorbed thereon a biologically active substance selected for its efficacy in diagnosing or treating the disease, and injecting the carrier into the body of a patient. For example, the carrier is injected by inserting delivery means into an artery to within a short distance from a body site to be treated and at a branch or branches (preferably the most immediate) to a network of arteries carrying blood to the site. The carrier is injected through the delivery means into the blood vessel. Just prior to injection, a magnetic field is established exterior to the body and adjacent to the site of sufficient field strength to guide a substantial quantity of the injected carrier to, and retain the substantial quantity of the carrier at, the site. Preferably, the magnetic field is of sufficient strength to draw the carrier into the soft tissue at the site adjacent to the network of vessels, thus avoiding substantial embolization of any of the larger vessels by the carrier particles.

It is therefore an object of this invention to provide an improved magnetically responsive composition for optionally carrying biologically active substances and methods of production and use thereof.

It is another object of this invention to provide a magnetically responsive carrier for biologically active substances which has improved magnetic responsiveness, yet is durable during storage and use, and includes up to about 20% by mass of a biologically active substance adsorbed thereon.

It is another object of this invention to provide a magnetically responsive composition comprising particles having a major dimension of from about 0.5 μm to about 5.0 μm, each iron:carbon composite particle including about 1.0% to about 95.0% by mass of carbon distributed throughout the volume of the particle.

It is still another object of this invention to provide a composition utilized for localized in vivo diagnosis or treatment of disease including a carrier with composite iron:carbon particles from about 0.5 μm to about 5.0 μm in size, each composite iron:carbon particle including carbon and iron with the carbon distributed throughout the volume of the particle, and an optional biologically active substance selected for its efficacy in diagnosing or treating the disease which is adsorbed on the particles.

It is yet another object of this invention to provide a method of producing a magnetically responsive carrier composition including composite iron:carbon particles including carbon and iron with the carbon distributed throughout the volume of each of the particles.

It is yet another object of this invention to provide liquid and dry kits for administering a composition utilized for localized in vivo diagnosis or treatment of disease including a ferrocarbon particle with an optional biologically active substance adsorbed thereon that has been selected for its efficacy in diagnosing or treating the disease.

It is a further object of this invention to provide methods of sterilization of the components of the kits supplied for administering a composition utilized for localized in vivo diagnosis or treatment of disease including a ferrocarbon particle with an optional biologically active substance adsorbed thereon that has been selected for its efficacy in diagnosing or treating the disease.

With these and other objects in view, which will become apparent to one skilled in the art from the following description, this invention resides in the novel construction, combination, arrangement of parts and methods substantially as hereinafter described, and more particularly defined by the appended claims, it being understood that changes in the precise embodiment of the herein disclosed invention are meant to be included as they come within the scope of the claims.

DESCRIPTION OF THE INVENTION

The magnetically controllable, or guided, carrier composition of this invention includes composite, volume-compounded ferrocarbon particles of about 0.1 μm to about 5.0 μm in average major dimension, and preferably between about 0.5 μm and about 5.0 μm, containing about 1.0% to about 95.0% by mass of carbon, for example, between about 10% and 60%. About 20% to about 40% is the preferred range of carbon having been found to exhibit characteristics useful in many applications.

The particles are produced by mechanically milling a mixture of iron and carbon powders, without application of external heat. The composite iron:carbon carrier particles so obtained may then be placed in a solution of a biologically active substance to allow adsorption of the biologically active substance to the particles. The composite particles are separated for desired size and magnetic susceptibility characteristics. Separation of the particles can occur before or subsequent to exposure to the biologically active substance.

Figure 1:
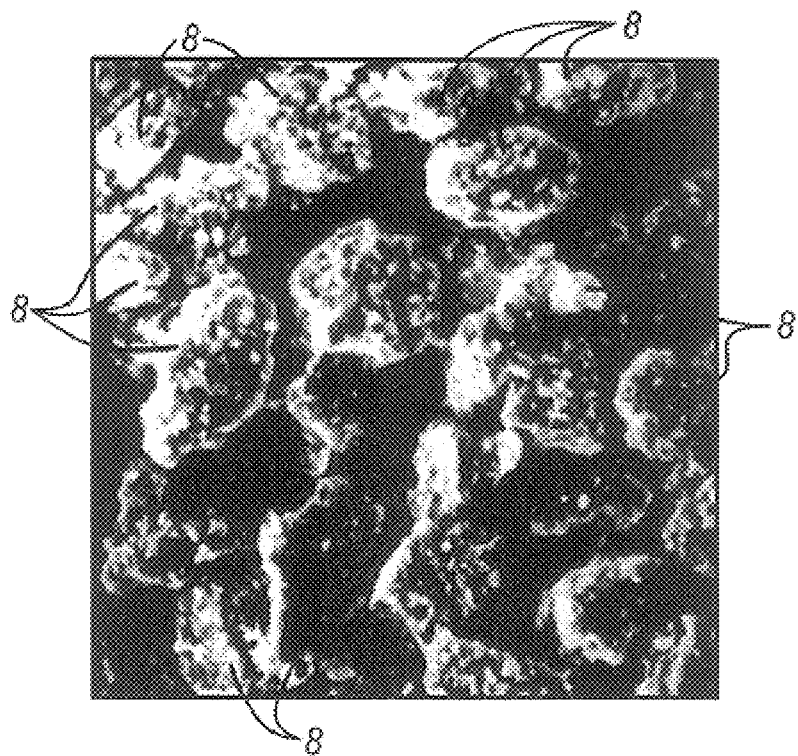
FIG. 1 is a magnified photograph (12000×) of composite particles of the carrier composition of this invention.
Figure 2A:
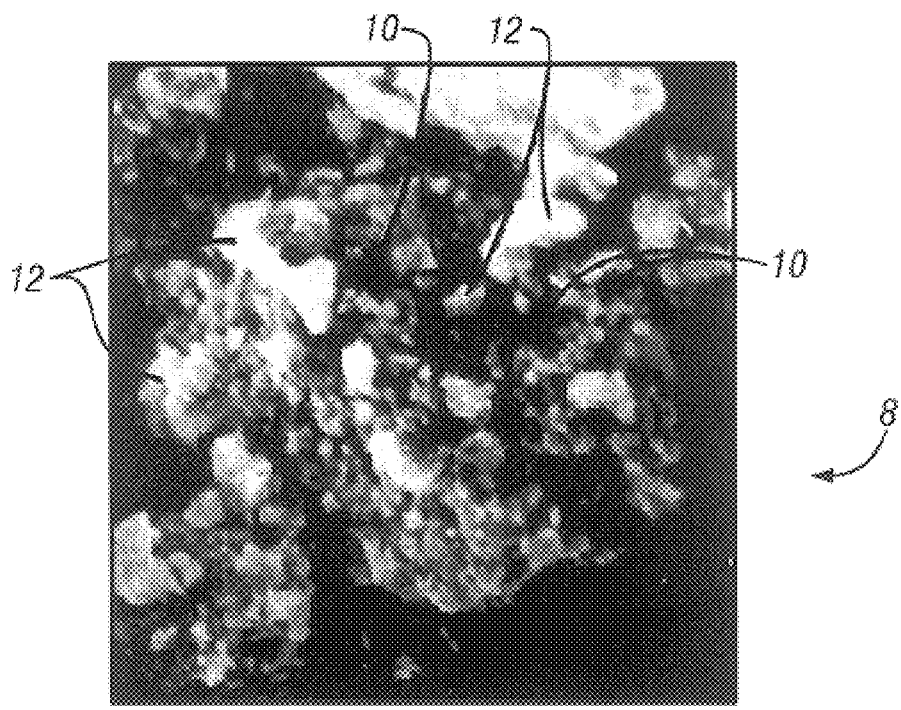
FIG. 2A is a magnified photograph (30,000×) of a particle of the carrier composition of this invention.

As shown in FIGS. 1 and 2A, iron:carbon particles 8 manufactured by the method of this invention are of a generally spherical shape, with the inclusions of carbon deposits 10 presumably being located throughout the whole volume of each particle (both at the surface and the interior of each particle). The strong connection between the components (iron 12 and carbon 10) which is not broken during prolonged storage of the magnetically controlled composition, its transportation, storing, packing and direct use. Chemical binding may take place between the iron and carbon, such as a trace interlayer of cementite ($Fe_3C$) formed during the milling process.

The iron:carbon particles are also useful as a carrier for delivering one or more adsorbed biologically active substances to specific body sites under control of an external magnetic field. As used herein, the term "biologically active substance" includes substances useful for in vivo medical diagnosis and/or treatment.

As used herein, the term "genetic material" refers generally to nucleotides and polynucleotides, including nucleic acids, RNA and DNA of either natural or synthetic origin, including recombinant, sense and antisense RNA and DNA. Types of genetic material may include, for example, genes carried on expression vectors, such as plasmids, phagemids, cosmids, yeast artificial chromosomes, and defective (helper) viruses, antisense nucleic acids, both single and double stranded RNA and DNA and analogs thereof, as well as other proteins or polymers.

For in vivo diagnostic imaging, the type of detection instrument available is a major factor in selecting a given radioisotope. The radioisotope chosen must have a type of decay that is detectable for a given type of instrument. Generally, gamma radiation is required. Still another important factor in selecting a radioisotope is that the half-life be long enough so that it is still detectable at the time of maximum uptake by the target, but short enough so that deleterious radiation with respect to the host is minimized. Selection of an appropriate radioisotope would be readily apparent to one having average skill in the art. Radioisotopes which may be employed include, but are not limited to $^{99}Tc$, $^{142}Pr$, $^{161}Tb$, $^{186}Re$, and $^{88}Re$. Additionally, typical examples of other diagnostically useful compounds are metallic ions including, but not limited to $^{111}In$, $^{97}Ru$, $^{67}Ga$, $^{68}Ga$, $^{72}As$, $^{89}Zr$, and $^{201}Tl$. Furthermore, paramagnetic elements that are particularly useful in magnetic resonance imaging and electron spin resonance techniques include, but are not limited to $^{157}Gd$, $^{55}Mn$, $^{162}Dy$, $^{52}Cr$, and $^{56}Fe$.

It is also noted that radioisotopes are also useful in radiation therapy techniques. Generally, alpha and beta radiation is considered useful for therapy. Examples of therapeutic compounds include, but are not limited to $^{32}P$, $^{186}Re$, $^{188}Re$, $^{123}I$, $^{125}I$, $^{90}Y$, $^{166}Ho$, $^{153}Sm$, $^{142}Pr$, $^{143}Pr$, $^{149}Tb$, $^{161}Tb$, $^{111}In$, $^{77}Br$, $^{212}Bi$, $^{213}Bi$, $^{223}Ra$, $^{210}Po$, $^{195}pt$, $^{195}Pt$, $^{255}Fm$, $^{165}Dy$, $^{109}Pd$, $^{121}Sn$, $^{127}Te$, and $^{211}At$. The radioisotope generally exists as a radical within a salt, however some tumors and the thyroid may take up iodine directly. The useful diagnostic and therapeutic radioisotopes may be used alone or in combination.

As a general principle, the amount of any aqueous soluble biologically active substance adsorbed can be increased by increasing the proportion of carbon in the particles up to a maximum of about 40% by mass of the composite particles without loss of utility of the particles in the therapeutic treatment regimens described in this application. In many cases it has been observed that an increase in the amount of adsorbed biologically active substance is approximately linear with the increase in carbon content. However, as carbon content increases, the susceptibility, or responsiveness, of composite particles 8 to a magnetic field decreases, and thus conditions for their control in the body worsen (although adsorption capacity increases). Therefore, it is necessary to achieve a balance in the iron:carbon ratio to obtain improved therapeutic or diagnostic results. To increase the amount of agent given during a treatment regimen, a larger dose of particles can be administered to the patient, but the particles cannot be made more magnetic by increasing the dose. Appropriate ratios may be determined by any person having average skill in the art.

It has been determined that the useful range of iron:carbon ratio for particles intended for use in in vivo therapeutic treatments as described in the application is, as a general rule, from about 95:5 to about 50:50, for example about 80:20 to about 60:40. The maximum amount of the biologically active substance that can be adsorbed in the composite iron:carbon carrier particles of any given concentration of carbon will also differ depending upon the chemical nature of the biologically active substance, and, in some cases, the type of carbon (i.e., activated carbon (AC)) used in the composition. For example, it has been discovered that the optimal iron:carbon ratio for carrier particles used to deliver adsorbed doxorubicin in in vivo therapeutic treatments is about 75:25.

However, adsorption of biologically active substances that are substantially insoluble in water (i.e., with solubility in water less than about 0.1% by weight) requires use of special procedures to adsorb a useful amount of a drug on the particles. Applicants have discovered that adsorption on the carrier particles of this invention of biologically active substances having substantial insolubility in water can be obtained without the use of surfactants, many of which are toxic, by dissolving the water insoluble biologically active substance in a liquid adsorption medium (e.g., aqueous) that includes excipients selected to minimize the hydrophobic Van der Waals forces between the particles and the solution and to prevent agglomeration of the particles in the medium. For example, if the biologically active substance is a highly non-polar molecule, such as camptothecin, and the adsorption medium is a highly non-polar liquid, such as chloroform-ethanol, the drug does not preferentially leave the adsorption medium to adsorb to the carbon. However, in a more polar adsorption medium, adsorption to the carrier particles is entirely acceptable. For example, binding of therapeutic levels of paclitaxel, a highly water-insoluble drug, to carrier particles having an iron:carbon ratio of 70:30 was obtained using citrated ethanol as the adsorption medium, even though paclitaxel is substantially water insoluble. In many cases, it is advantageous if the liquid adsorption medium includes a biologically compatible and biodegradable viscosity-increasing agent (e.g., a biologically compatible polymer), such as sodium carboxymethyl cellulose, to aid in separation of the particles in the medium.

Using the methods of this invention, doxorubicin has been adsorbed onto carrier particles having iron:carbon ratios from 80:20 to 60:40 (Type A activated carbon) in amounts in the range from about 0.0% to about 20% of the mass of the particles on average. Example 5 illustrates the formulation of excipients useful for enhancing adsorption of doxorubicin to the carrier particles. Other biologically active agents may also be adsorbed using similar techniques that would be obvious to any person having average skill in the art.

Because it is convenient to prepare and market the carrier particles in a dry form, the excipients may be prepared in dry form, and an adsorption-enhancing amount of one or more dry excipients useful for solubilizing the drug or other biologically active substance when in a liquid solution are packaged together with a unit dose of the carrier particles. An adsorption-enhancing amount of the dry excipients will be determined by one of skill in the art depending upon the chemical properties of the biologically active substance as needed to overcome the chemical forces that cause insolubility of the biologically active substance of interest and agglomeration of the particles in aqueous solution. Most preferably, the package or kit containing both the dry excipients and dry carrier particles is formulated to be mixed with the contents of a vial containing a unit dose of the drug and sufficient amount of a biologically compatible aqueous solution, such as saline, as recommended by the drug manufacturer, to bring the drug to a pharmaceutically desirable concentration. Upon mixture of the solution containing the dilute drug with the contents of the kit including the dry components (i.e., the dry carrier particles and dry excipients), the drug is allowed to adsorb to the carrier particles, forming a magnetically controllable composition containing a therapeutic amount of the biologically active substance adsorbed to the carrier particles that is suitable for in vivo therapeutic or diagnostic use.

Alternatively, a liquid kit may be employed. Here, the carrier particles are contained as one unit, for example, in a vial, while the aforementioned excipients are contained in another unit in the form of an aqueous solution. At the time of administration, the ferrocarbon particles are mixed with the contents of a vial containing a unit dose of the drug and sufficient amount of a biologically compatible aqueous solution, such as saline, as recommended by the drug manufacturer, to bring the drug to a pharmaceutically desirable concentration. Subsequently, the resulting particles having the biologically active substance adsorbed thereon, are mixed with yet another unit containing the excipients in aqueous solution. Any suitable sterilization technique may be employed. For example, the ferrocarbon particles may be sterilized using gamma irradiation and the aqueous solution of excipients may be sterilized by autoclave. Use of autoclave undesirably oxidizes the ferrocarbon particles.

A diagnostic or therapeutic amount of biologically active substance adsorbed to the carrier particles will be determined by one skilled in the art as that amount necessary to effect diagnosis or treatment of a particular disease or condition, taking into account a variety of factors such as the patient's weight, age, and general health, the diagnostic or therapeutic properties of the drug, and the nature and severity of the disease.

A number of considerations are involved in determining the size of carrier particles to be used for any specific therapeutic situation. The choice of particle size is determined in part by technological constraints inherent in producing the particles under 0.2 $\mu$m in size. In addition, for particles less than about 1.0 $\mu$m in size, the magnetic control in blood flow and the carrying capacity is reduced. Relatively large particle sizes can tend to cause undesirable embolization of blood vessels during injection either mechanically or by facilitating clot formation by physiological mechanisms. The dispersion may coagulate, which makes injections more difficult, and the rate at which biologically active substances desorb from the particles in the targeted pathological zones may decrease. The method (such as is described below) of milling together a mixture of iron and carbon powders produces an approximately spherical form with a granular surface for the particles, and results in a particle population having an average major dimension of about 0.1 $\mu$m to about 5.0 $\mu$m.

Because the iron in the particles described in this invention is not in the form of an iron oxide, as is the case in certain previously disclosed magnetically controlled dispersions, the magnetic susceptibility, or responsiveness, of ferrocarbon particles 8 is maintained at a high level.

Figure 2B:
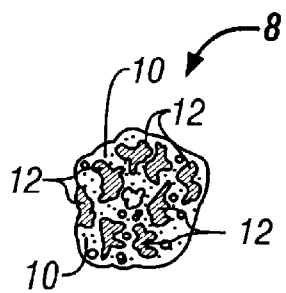
FIG. 2B is a sectional illustration of the particle of FIG. 2A.

The iron:carbon particles are characterized by a well-developed substructure (see FIG. 2B), having a connected network of iron forming a network of voids with carbon deposits 10 captured therein. The characteristic substructure of the particles formed during the process of joint deformation of the mechanical mixture of iron and carbon powders, also increases the magnetic susceptibility of iron inclusions in ferrocarbon particles 8 as compared with iron particles having other types of substructure. For example, the composite ferrocarbon particles produced by the herein suggested method have greater magnetic susceptibility than the particles disclosed in European Patent Office Publication No. 0 451 299 Al, although the ferromagnetic content in both types of particles is about the same. This high magnetic responsiveness of ferrocarbon particles 8 makes it possible, in some cases, to utilize magnetic fields lower than about 250 gauss to position the particles at the desired anatomical site.

Because of the large surface of carbon deposits 10 in particles 8, the adsorbed biologically active substance comprises up to about 20.0% by mass of particles 8; or, in different terms, up to about 200 mg of adsorbed biologically active substance per gram of particles 8. Therefore, in use, much less of the carrier is injected to achieve a given dose of the biologically active substance or, alternatively, a higher dosage of the biologically active substance per injection is obtained than is the case with some previously known carriers.

The following describes a method for producing small quantities of the ferrocarbon composition of this invention, it being understood that other means and mechanisms besides milling could be conceived of for jointly deforming iron and carbon powders, which comprise the essential starting elements for production of the carrier. The procedure utilized exerts mechanical pressure on a mixture of carbon and iron particles to deform the iron particles and develop a substantial substructure, which captures the carbon. The formation of the ferrocarbon particles is accomplished without the addition of heat in the process (although the mixture heats up during the mechanical deformation step), and is conducted in the presence of a liquid, for example ethanol, to inhibit oxidation of the iron and to assure that the particles produced are clean (sterile). The liquid may also serve as a lubricant during the milling of the iron and carbon powder, and may reduce compacting of carbon during processing. As a result, the density of the carbon deposits in the composition is maintained so as to maximize adsorption capacity of the particles.

For example, to produce particles having an average of about 75:25 iron:carbon ratio by mass, one part of substantially pure iron particles having average diameters from 0.1 $\mu$m to 5 $\mu$m in size are mixed with about 0.1 to 1.0 parts by weight of substantially pure carbon granules (typically about 0.1 $\mu$m to 5.0 $\mu$m in diameter). The iron particles and carbon granules are mixed vigorously to achieve good distribution throughout the volume. Preferably the carbon granules are activated carbon. Each biologically active substance should be evaluated individually with the various types of carbon in order to determine the optimum reversible activated carbon binding. Factors such as pH, temperature, particulate size, salts solution viscosity and other potentially competing chemicals in solution can influence adsorption capacity, rate, and desorption parameters. Activated carbon types which are useful include, but are not limited to A, B, E, K and KB and chemically modified versions thereof.

The mixture is put into a standard laboratory planetary ball, or attrition mill of the type used in powder metallurgy. For example, the mill can have 6 mm diameter balls. An appropriate amount of a liquid, for example ethanol, is added for lubrication. The mixture is milled for between 1 and 12 hours, or for the time necessary to produce the particles heretofore described. Depending on the mill used, the speed of the mill may be anywhere in the range from about 120 rpm to about 1000 rpm (typically about 350 rpm), the process not being overly sensitive to the speed of the mill.

After joint deformation of the iron:carbon mixture, the particles are removed from the mill and separated from the grinding balls, for example, by a strainer. The particles may be resuspended in ethanol and homogenized to separate the particles from each other. The ethanol is removed, for example, by rotary evaporation, followed by vacuum drying. Any suitable drying technique may be employed. Particles should be handled so as to protect against oxidation of the iron, for example, in a nitrogen environment.

After drying, the particles should be collected according to appropriate size. For example, the particles may be passed through a 20 $\mu$m sieve and collected in an air cyclone to remove particles larger than 20 $\mu$m. The cyclone only collects particles of a certain size and density, providing a method for removing fines and loose carbon. The sieved particles may be packaged under nitrogen and stored at room temperature.

Particles may be subaliquoted into dosage units, for example, between 50 and 500 $\mu$g per dose, and may be further overlayed with nitrogen, for example. Dosage units may be sealed, for example, with butyl rubber stoppers and aluminum crimps. Dosage units may then be sterilized by appropriate sterilization techniques, for example, gamma irradiation between 2.5 and 3.5 Mrads.

When ready for use, or before packaging if the carrier is to be prepared with a preselected biologically active substance already adsorbed thereon, about 50 mg to 150 mg (about 75 mg to about 100 mg is preferred to be absolutely assured of maximum adsorption) of the biologically active substance in solution is added to I gram of the carrier. When ready for application to a patient, the combination is placed into suspension (for example, in 5 to 10 ml) of a biologically compatible liquid such as water or saline utilizing normal procedures.

Experimental evidence shows increased therapeutic efficacy on a tumor growth with the use of the magnetically controlled carrier composition of this invention with an anti-tumor preparation in comparison with previously known magnetically controlled dispersions.

EXAMPLE 1

Tests were carried out on male rats of the Wistar Line (bred at Stolbovaya Station of the USSR Academy of Medical Sciences). The rats were infused with carcinosarcoma Walker 256 under the tail skin. When the tumorous volume averaged 986±98 mm$^3$ the animals were divided into 4 groups, 10 rats in each. The first group (group I) was a control group, and groups II through IV were experimental groups.

The animals in group II were given intravenous injections of a water solution of rubomicine in the amount of 2 mg/kg of body weight during 5 days (the model of traditional use of such anti-cancerous preparations in clinics). The rats in group III were injected with a suspension of ferrocarbon dispersion produced by the previously known method described in European Patent Office Publication No. 0 451 299 A1. The particles comprised iron/carbon in a volume percent ratio of 60:40. The dosage of ferrocarbon particles was 160 mg/kg of body weight, and the dosage of adsorbed rubomicine thereon was 3.2 mg/g of particles. This suspension was injected into the tail vein after placing on the surface of the tumor a permanent magnet with a magnetic field intensity of 6000 oersteds. Localization of the suspension in the tumorous growth zone under control of the externally placed magnetic field was monitored by x-ray pictures.

Using the same techniques for injection and magnetic localization, including placement of a permanent magnet with a magnetic field of 600 oersteds on the surface of the tumor and monitoring. The animals from group IV were given a one-time intravenous injection of the magnetically controlled dispersion produced in accord with the methods of this invention localization of the particles was observed by x-ray. The dosage was 160 mg of carrier particles per/kg of carrier particles of body weight. The combination of iron:carbon in individual particles of the dispersion was in percent ratio of 60:40, which was similar to the ratio in the dispersion produced by the previously known method used in experimental group III.

Due to the improved adsorptive capability of particles 8, the dose of rubomicine adsorbed on the magnetically controlled carrier particles of this invention was 9.96 mg of rubomicine per/g of particles, which was 3.1 times more than the rubomicine adsorbed by the previously known carrier particles in the experiment with the rats of group III. This result was achieved solely due to the relative specific adsorption capacities of the given carrier particles.

Observation of the animals gave the following results. The life span of animals in control group I averaged 21±1.5 days. In group II, as a result of prescribed intravenous injections of the water solution of rubomicine, to model the traditional use of anti-tumor drugs in the clinic, the life span of the rats following treatment increased by an average of 4.5 days (P<0.05). The animals from experimental group III lived for an average of 46±4.3 days following treatment, which was 2.2 times more (P>0.001) than the life span of the control animals.

In group IV, 6 rats out of 10 (i.e., 60% of the cases) demonstrated complete dissolution of the tumor, which took place during 5 to 7 days after the one-time injection of the suspension of the magnetically controlled composition. Moreover, the remaining 4 rats from this group lived an average 57.4±5.9 days after treatment, thus exceeding the life span of the animals from group III by 25.0%. Their average life span post treatment was also 2.7 times longer than that of the rats from control group I. The animals from group IV that showed complete regression of the tumors did not see any recurrence of tumorous growth during 157 days of observation, which is a result consistent with complete elimination of the tumors in these rats.

EXAMPLE 2

Figure 4:
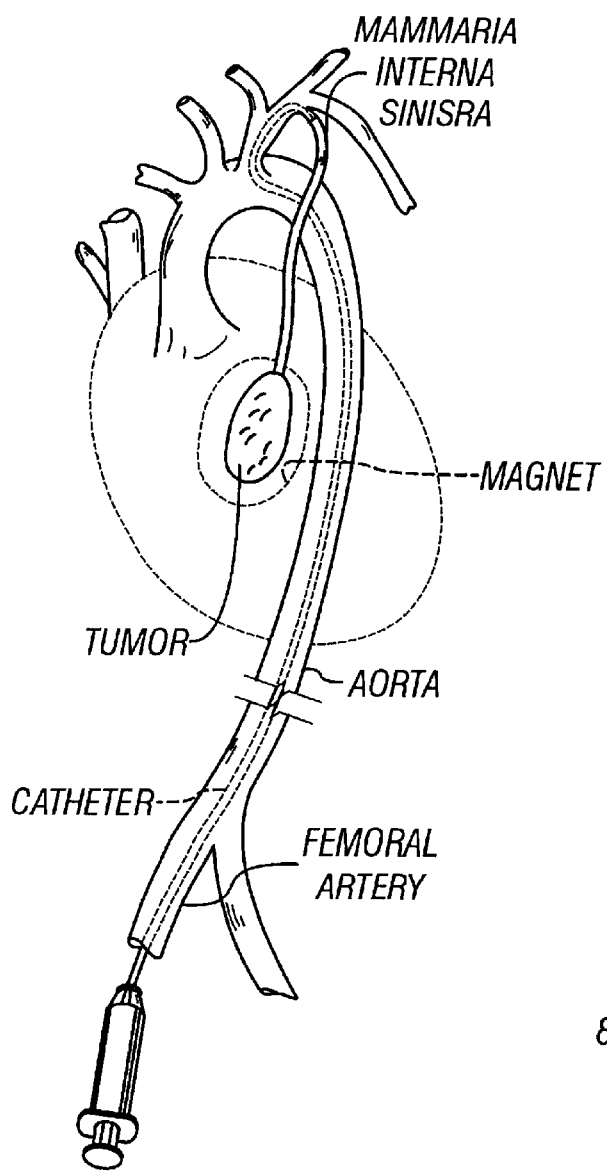
FIG. 4 is a diagram illustrating one example of application and magnetic targeting of the carrier composition.
Figure 5:
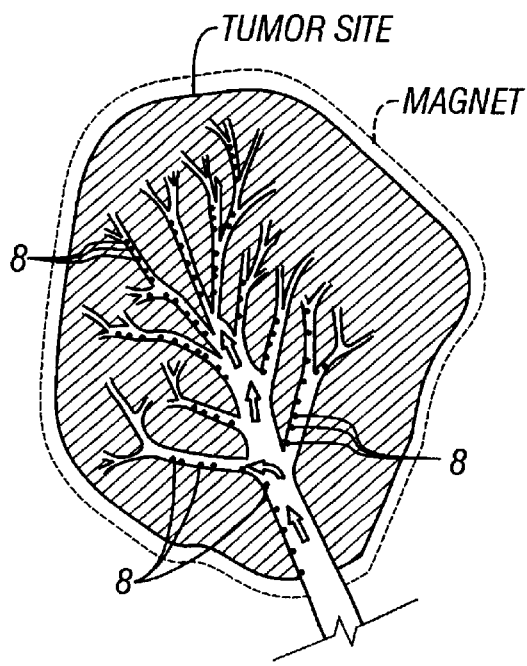
FIG. 5 is a diagram illustrating the carrier composition (having a drug adsorbed thereon) at a pathological structure.

Further clinical observation has documented the effectiveness of this invention. FIGS. 4 and 5 illustrate use of this invention for treatment and observation of a 61 year-old woman admitted on Feb. 13, 1992, to the Zil Hospital in Moscow, Russia (CIS) and diagnosed with cancer of the left mammary gland $T_3N_1M_1$.

The diagnosis was first made in 1989 when a biopsy was done. In December, 1991, focal radiation therapy (10 grey) resulted in the tumor being partially reduced. The decision was made to use chemotherapy in the forms of the intra-arterial selective localization of the carrier of this invention with doxorubicin (Adriamycin® as the biologically active agent adsorbed on the carrier.

Figures 3A, 3B:
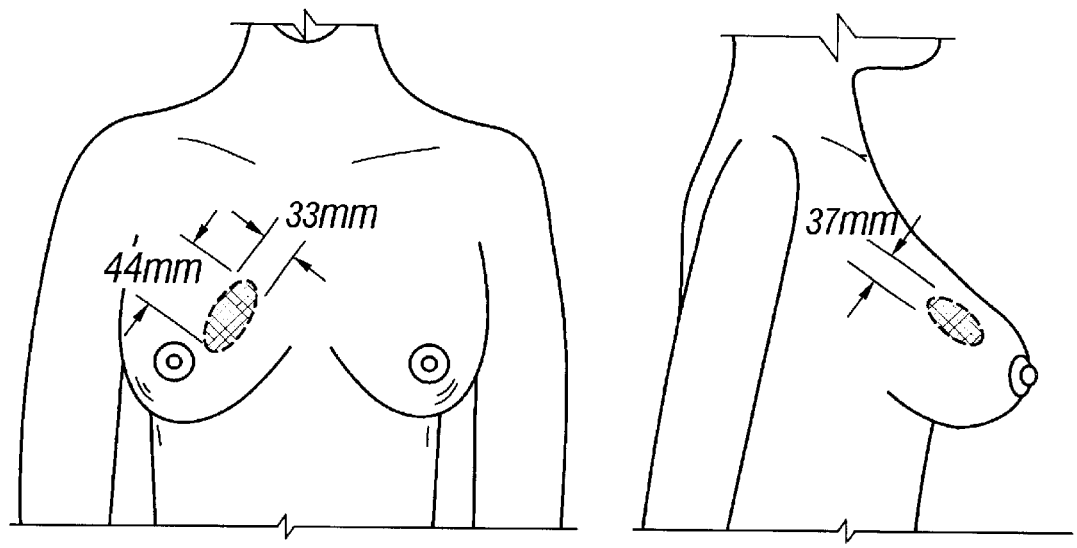
FIGS. 3A through 3H are illustrations of a tumor during periods of treatment utilizing drugs adsorbed on the carrier composition and delivered to, and maintained at, the tumor site utilizing one method of this invention.

Before the treatment, the dimensions of the tumor (illustrated in FIGS. 3A and 3B) were 44 mm×33 mm×37 mm (65 mm×45 mm, manual). On Feb. 24, 1992, a femoral artery (FIG. 4) was punctured and a vascular catheter was inserted into the aorta according to the Seldinger method under local anaesthesia (0.5% novocaine, 30 ml). Under roentgenologic and contrast control, the catheter was placed at 25 mm distance from the branch to the left intra-pectoral artery (a. mammaria interna sinisra). A newly prepared suspension of gelatinol with ferrocarbon particles 8 having 15 mg doxorubicin (Adriamycin®) adsorbed thereon was injected through the catheter. At this time, a magnet having a magnetic field intensity of 15,000 oersteds was placed over the tumor for 20 minutes. As a result, the injected suspension was kept localized by the magnetic field in the zone of the tumor for 20 minutes (a time sufficient for full microembolization of the tumor feeding capillaries). The patient's condition was satisfactory at the time of therapy.

Figures 3C, 3D:
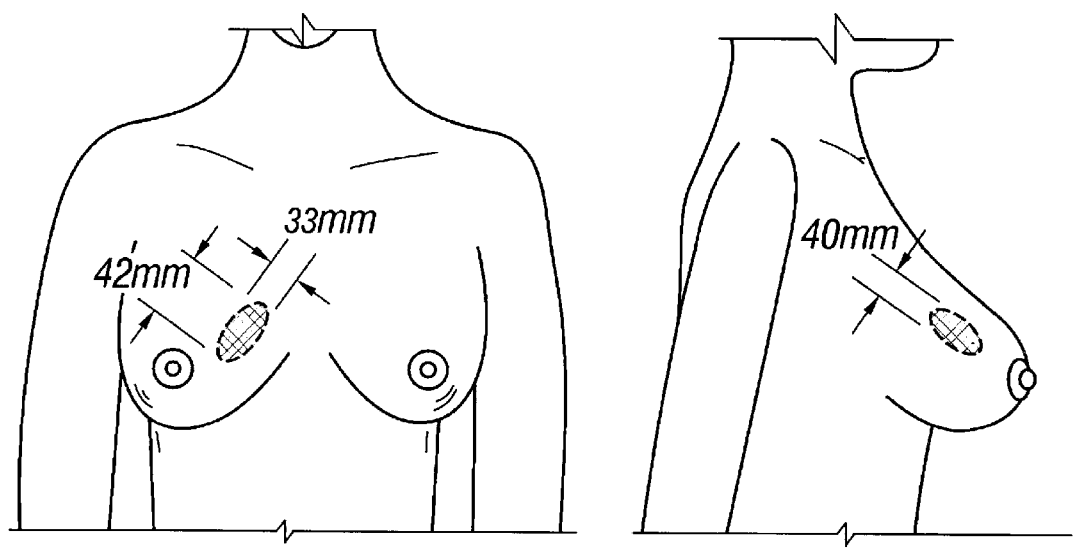
Figures 3E, 3F:
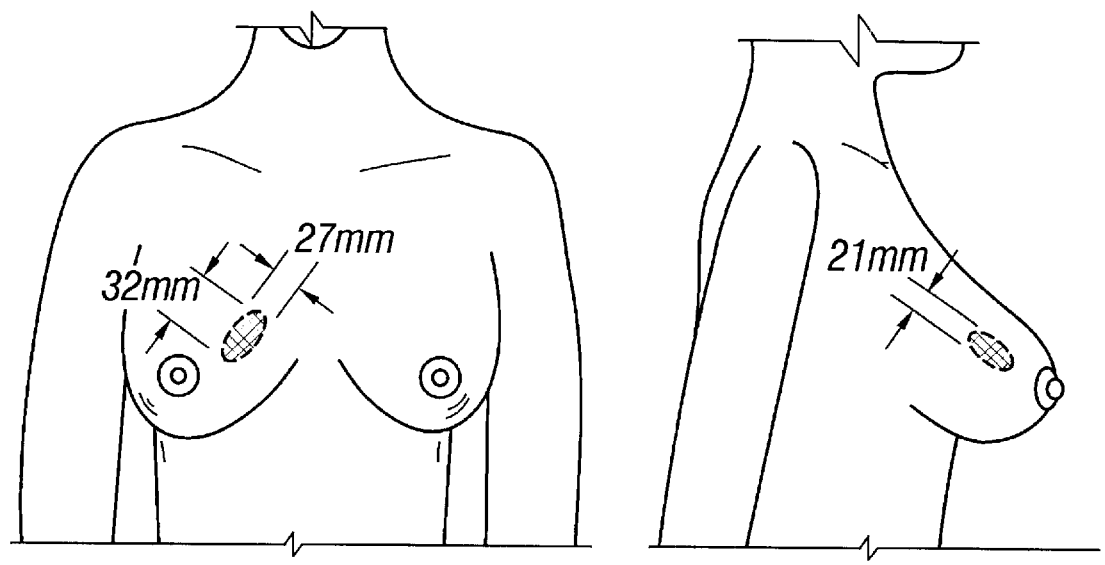
Figures 3G, 3H:
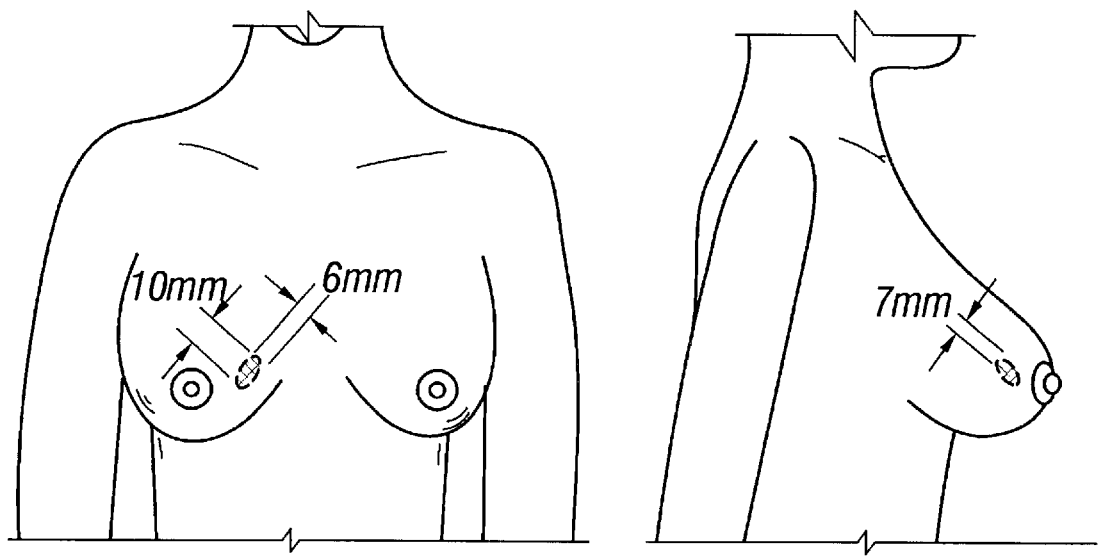

By Feb. 28, 1992, the patient's condition had improved. An ultrasonic examination of the left mammary gland showed the dimensions of the tumor at 42 mm×33 mm×40 mm as shown in FIGS. 3C and 3D. The tumor had a legible contour. By Mar. 12, 1992, the dimensions of the tumor had been reduced by 66.3% to 32 mm×27 mm×21 mm (FIGS. 3E and 3F). By Apr. 14, 1992, the dimension had been reduced by 99.22% to 10 mm×6 mm×7 mm (FIGS. 3G and 3H).

It is believed that by releasing the carrier immediately upstream of the tumor (or other pathological) site, rather than penetrating the tumor, equally effective application of the biologically active substance occurs while potentially benefitting the patient by limiting spread of disease occasioned by puncture of the tumorous tissue. While a larger magnetic field was utilized in the above example of treatment, it has been found that the carrier composition of this invention begins to react in a field as small as 250 oersteds/cm (many prior art carriers needing a field as large a 500 oersteds/cm before being influenced).

FIG. 5 illustrates what is believed to occur under magnetic control at the treatment site. Under the influence of the applied magnetic field, the carrier particles are induced into the capillary network feeding the tumor. The particles are drawn closely adjacent to the soft tissue of the lumen of the capillaries (or perhaps even into the soft tissue) thereby reducing or eliminating the potential for embolization of the vessels by the carrier particles. The biologically active substance is released from the carrier particles by a dynamic process in which the substance in the carrier is replaced by materials produced by the body. For example the necrotic products of the tumor itself, may replace the biologically active substances, becoming adsorbed on the carrier particles such as proteins, glucose, lipids, peptides, or the like. Thus, the biologically active substance is literally pushed out of the carrier particles.

Typically, less than about 10% of the biologically active substance is replaced by body materials in the blood stream. Therefore, it is believed that the replacing substance must have a higher specific gravity than that of the biologically active substance. A small amount of the particles may not be attracted to the treatment site by the magnetic field or escapes from the treatment site. This fraction may also therapeutically active against tumor cells in the blood and elsewhere. In some cases, reduction in metastasis has been observed following treatment according to the method of this invention. Since the carrier composition is formed of material that is biodegradable or can be readily metabolized by the body, all carrier particles are excreted or metabolized, perhaps within 30 days of application.

As may be appreciated, an improved magnetically responsive carrier for biologically active substances and methods for producing and using the same are provided by this invention. The carrier particles exhibit improved responsiveness to magnetic fields, have improved drug adsorptive capacity, and are more durable during storage and use.

EXAMPLE 3

Recently a series of fluoroscopically-guided organ imaging studies were conducted in a porcine animal model using radioactive technetium (Tc) adsorbed to the carrier particles of the invention as the imaging agent. In order to evaluate physical chemical properties and interaction of Tc with carbon (C) and the iron:carbon carrier particles, rhenium (Re) was used as a non-radioactive surrogate for Tc. Re is a group VIIB element just below Tc in the periodic table. It has two artificial isotopes, $^{186}$Re and $^{188}$Re, which have half-lives longer than that of Tc and emit about the same gamma radiation as shown in Table 1 below:

TABLE 3

| Isotope source | t½ in hours | Gamma energy (keV) |
|---|---|---|
| $^{99}$Tc artificial | 7 | 140 |
| $^{186}$Re artificial | 90 | 137 |
| $^{188}$Re natural | 17 | 155 |

An adaptation of a colorimetric Re assay used in the field of metallurgy was used to determine the adsorption of the Re onto carrier particles having a 70:30 iron:carbon ratio. In brief, a 0.1 to 0.5 ml sample was placed in a solution containing 1.0 ml of HCl, 1.3 ml of –α furildoxime (6% in acetone), 0.5 ml of 10% stannous chloride and sufficient water to make 5.0 ml. The mixture was heated to 45° C. for 20 minutes and allowed to cool to room temperature. The absorbance of Re in the solution was measured at 532 nm. The sensitivity of the assay was to about 5 mcg Re. These studies indicated that Re binding to a series of carbons varies from about 35% at 30 mg carbon in the adsorption medium to about 90% at 180 mg carbon when incubated at ambient temperature. As with other drugs, the % binding of Re in the adsorption medium decreases as the Re to carbon ratio increases. However, the binding of Re to carbon does not correspond to the equilibrium binding isotherm of Langmuir, and it is independent of temperature and pH. Release over 24 hours of the Re into physiological saline at ambient temperature from the various carbons preloaded with adsorbed Re was 50% by weight.

Re was adsorbed onto carrier particles having iron:carbon ratios of 70:30 and 85:15, respectively, by incubating the particles at ambient temperature in an absorption medium containing buffered sodium chloride. Binding of the Re to the particles was determined by spectrophotometric assay. These studies showed that binding of Re to carrier particles increased with an increase in the ratio of carbon (i.e., in the particles) to Re in the adsorption medium. The useful amount of adsorbed radioisotope will vary depending upon the particular results desired, for example, from 10 pgm to 700 ng. The proper amount should be easily determinable by any person having average skill in the art. The binding parameters of for two different compositions iron:carbon carrier particles is shown in Table 2 below:

TABLE 2

| Iron:carbon ratio of particles | Amount of particles (mg) | Re ($\mu$g) in medium | Binding % | Q (ng/mg) |
|---|---|---|---|---|
| 85:15 | 100 | 140 | 25.9 | 360 |
| 70:30 | 100 | 140 | 40.3 | 560 |

Less than 10% of the Re was released upon incubation under efflux conditions in saline over 24 hours. The low binding of Re to the carrier particles is consistent with the low binding of other charged, small ionic molecules to activated carbon as compared with the high affinity binding of hydrophobic aromatic molecules. These findings are consistent with use of the carrier particles of the invention with adsorbed Re or Tc as imaging and therapeutic agents.

EXAMPLE 4

Carrier particles having a 80:20 iron:carbon ratio were prepared as described above. Adsorption upon the particles of various types of pharmaceutical agents at a range of concentrations of the pharmaceutical agent in the absorption solution was performed to determine the absorption curves and absorption constants for each compound as follows:

A. Antisense Oligonucleotide

A 16-mer anti-C-Myc oligonucleotide useful in antisense gene-directed therapy is an all phosphorothioate oligodeoxynucleotide, fluorescein-labeled at 5' end (Macromolecular Resources, Fort Collins, Colo.). The oligo was dissolved in a stock adsorption solution made in TE buffer (10 mM Tris-HCl, 1 mM EDTA, pH 8.0). The concentration of the oligonucleotide in the buffer was determined assuming 1 $AU_{260}$=33 $\mu$g of the oligo, according to the manufacturer's recommendations. Unbound drug in adsorption supernatants was determined from the fluorescein fluorescence (Exc. 495 nm, em. 549 nm) using a standard curve.

B. A Photosensitizer

Hematoporphyrin dihydrochloride (Sigma Chemical, USA, H-1875, Lot #23H0879) is a photosensitizer useful in tumor therapy. The compound accumulates by biological processes in certain types of tumor tissue. Upon exposure to light, such as provided by a laser, the compound undergoes a chemical transformation to produce oxygen singlets that are toxic to cells in which it has accumulated. A stock adsorption solution was prepared and drug concentration was determined by spectrophotometry according to G. Garbo et al. *Anal. Biochem.* 151:70–81, 1985, which is incorporated herein by reference in its entirety. $\xi_{403}$=327 $mM^{-1}$ in 1 N HCl). Unbound drug in adsorption supernatants was determined by spectrophotometry in an adsorption solution of 1 N HCl. The adsorption equation determined by computer analysis using commercially available software was: C ($\mu$g/ml)=0.0984$A^2$+1.85A at 403 nm.

C. An Anti-inflammatory Agent

6-Mercaptopurine sodium salt (provided by Dr. Gruber, Burroughs Wellcome, Lot #7P2774) is an anti-inflammatory agent. A stock adsorption solution was prepared by dissolving contents of a vial containing the compound in 10 ml of MilliQ water. Drug concentration in adsorption supernatants was determined by spectrophotometry (standard curve: C ($\mu$g/ml)=9.0A −0,035 at 311 nm, R=0.9999, in 0.9% NaCl, pH adjusted to 10.4 with NaOH).

D. An Anti-fungal Agent

Amphotericin B (Sigma Chemicals, A-4888, Lot 64H4005) is a therapeutically active agent useful against fungal infections. A stock solution was prepared in 0.9% NaCl, 10 mM KOH at pH 12, with concentration derived from drug weight corrected for the main compound content (80%). Drug concentrations in adsorption supernatants determined by spectrophotometry yielded the following equation for the concentration curve: C ($\mu$g/ml)=3.61$A^2$+ 18.1A+0.14 at 403 nm, R=0.9997, in 0.9% NaCl, 10 mM KOH.

E. An Anti-cancer Agent

Camptothecin (Sigma Chemicals, C-991 1, Lot #34140956) is an anti-proliferative agent useful in treatment of certain types of tumor. A stock solution of 2 mg of camptothecin per ml was formed by dissolving the precise weight of the drug in the mixture of chloroform and ethanol at a ratio of 1:1 by volume (C/E 1:1). Drug concentration in adsorption supernatants as determined by spectrophotometry yield the following equation for the concentration curve: C ($\mu$g/ml)=(16.7±0.26)A at 360 nm in C/E 1:1.

Camptothecin was also dissolved in DMSO and 0.9% saline solution, pH 3.0 at 1 mg/mL. Concentration was determined by absorbance at 253 nm ($\lambda_{max}$=253 nm in saline solution). Dilutions were made with 0.9% saline solution and MTC particles added to determine the Langmuir binding isotherm.

The adsorption parameters determined are summarized in Table 3 following:

TABLE 3

| Drug | Iron:carbon ratio | Adsorption medium | Equilibration time (hrs) | Maximum adsorption (% of carrier weight) | Adsorption constant $(mg/ml)^{-1}$ |
|---|---|---|---|---|---|
| Oligonucleotide | 80:20 Type K | TE buffer | 1 | 1.48 ± 0.10 | $(1.0 ± 2.1)10^{-2}$ |
| Oligonucleotide | 80:20 Type K | HEPES-$NS^1$ | 2 | 5.42 ± 0.34 | $(3.4 ± 2.3)10^{-2}$ |
| Hematoporphyrin | 80:20 Type K | 0.9% NaCl | 1 | 5.97 ± 0.24 | $(3.0 ± 1.8)10^{-4}$ |
| 6-MP Mercaptopurine | 80:20 Type K | 0.9% NaCl, pH 10.4 | 2 | 11.0 ± 0.97 | 0.24 ± 0.064 |

TABLE 3-continued

| Drug | Iron:carbon ratio | Adsorption medium | Equilibration time (hrs) | Maximum adsorption (% of carrier weight) | Adsorption constant $(mg/ml)^{-1}$ |
|---|---|---|---|---|---|
| Amphotericin B | 80:20 Type K | 0.9% NaCl pH 12 (KOH) | 24 | 10.4 ± 0.55 | $(1.1 ± 0.4)10^{-2}$ |
| Camptothecin | 80:20 Type K | C/E 1:1 | 3 | $0^2$ | — |
| Camptothecin | 75:25 Type K | Saline solution | 0.5 | 11 | 521 |

[1] 0.15 M NaCl, 20 mM HEPES-Na, pH 7.4
[2] Below detection limit

The results in Table 3 show that binding of the drug to the carrier particles is highly influenced by the composition of the adsorption solution or medium. Camptothecin is a highly non-polar molecule. In a highly non-polar adsorption medium (chloroform-ethanol), the drug does not preferentially leave the adsorption medium to adsorb to the carbon. However, in a more polar adsorption medium, it is believed that adsorption to the carrier particles would be entirely acceptable. One of the factors that influences the adsorption of the drug in the adsorption medium to the carbon in the carrier particle is the hydrophobic Van der Waals interactions between the drug and the particles. Alternatively, the drug can be dried onto the particles by evaporation techniques, for example, for adsorption of paclitaxel (PAC).

EXAMPLE 5

The carrier particles used for adsorption of paclitaxel (PAC) have an iron:carbon content of 70:30. The carbon is activated carbon type E. To analytically determine the iron content the following procedure was used. A portion of the sample was weighed (previously dried in a vacuum desiccator) and washed at 2000° C., oxidizing all carbon and iron present. During this procedure carbon was converted quantitatively to $CO_2$ and volatilized, leaving a residue of $Fe_2O_3$. The iron content was calculated by the formula. $Fe=Fe_2O_3/1.42977$, assuming no $Fe_2O_3$ was present initially. Carbon was assumed to be the remaining fraction. A second analysis of another portion of the sample was performed on a LECO carbon combustion analyzer. The sample was combusted and the $CO_2$ then measured, and total carbon was calculated. Iron and carbon content calculated by both methods gave comparable results of about 69% by weight of elemental iron.

A. Binding properties of Paclitaxel to Composite Particles

Drug adsorption was measured in two ways: 1) Initially a UV spectrophotometric assay was developed for screening drug bound to a variety of activated carbons. HPLC or spectrophotometric grade solvents were used throughout. The $\lambda_{max}$ in ethanol was determined to be 220 nm. A Milton Roy Spectronic 21 spectrophotometer was used with 3 mL quartz cells. The wavelength of 254 nm was selected for UV analysis because it provided good sensitivity for the drug. Little or no contamination from various assay techniques or materials was found at that wavelength. The same wavelength was used for the HPLC analysis. The UV assay was linear for paclitaxel over the range 0.05–3.0 mg/mL.

In one test the carrier particles contained the KB-type carbon. It has a small pore size (~40 nm effective radius), >1000 $m^2$/gm surface areas, and good hardness. PAC adsorption capacity however was limited. A survey of some 20 other candidate activated carbons was reduced to three types with promising drug delivery properties, A, B, and E types of carbon. Iron powder alone was also tested. Each of these materials was used at a concentration of 30 mg in citrated ethanol. The analysis by UV methods gave the following binding results for 3 mg of PAC. Type A carbon—74%, Type B carbon=65%, Type E carbon=33%, and iron powder=0% (no binding) Types A and B carbon are both large pore, large surface area (≧180 0$m^2$/gm) carbons with drug release characteristics equivalent to the E-type. E-type is a much harder carbon with a smaller surface area and consequently better milling properties.

B. Paclitaxel Binding to Different Activated Carbons

Fractional binding (fb) (amount bound of initial amount of PAC) to activated carbon types A, B, and E increased with increasing amount of carbon (at fixed PAC concentration). Types A and B carbon could be shown to bind PAC 100% and to plateau in the binding curve at high activated carbon content. Fractional bind of Type E was only 68%. The binding capacity, Q (expressed as % weight/weight drug carrier) was shown to decrease with an increase in the amount of activated carbon. For type A carbon, the binding capacity, Q, increased from 8% to 44% for a decrease in carbon from 40 mg to 5 mg. The corresponding Q value for AC type E was about 5% to 7%.

Other studies of drug binding to type A carbon have suggested that a plateau in the fraction of drug bound as a function of the amount of absorber is a result of multilaminar drug coating on the surface of the carrier. In contrast, a linear increase in fraction bound is indicative of unilaminar coating, thus in keeping with the rules of the Langmuir isotherm analysis.

Our studies showed that Types A and E carbon have the ability to adsorb a considerable fraction (fb) of PAC in the adsorption medium and that their binding capacity, Q, is also significant. On the other hand, carrier particles having a iron:carbon ratio of 70:30 (type E carbon) had both reduced capacity and fractional binding. These reduced values are in keeping with the proportionally lower carbon content of the carrier particles as compared with carbon alone. In contrast, both the fb and Q values for the carrier particles with a higher binding capacity type A carbon were less than 2%. This may be due to the inability of the pores in the carbon to withstand the compressive forces of the attrition milling process during manufacture.

Despite the extensive binding of activated carbon Types A and B to PAC, use of Type E carbon in carrier particles was preferred due to commercial availability, and the proper balance between binding and release properties. In addition, Type E carbon is the preferred activated carbon for use in a drug carrier because it has been established to have U.S. Pharmacopoeia (22nd edition) quality. FIG. 6 shows Langmuir adsorption plots for PAC binding to (-○-) carrier particles with an iron:carbon ratio of 70%:30% Type E carbon and (-□-) Type E carbon alone. Data were fit by simple unweighted linear regression.

Figure 6:
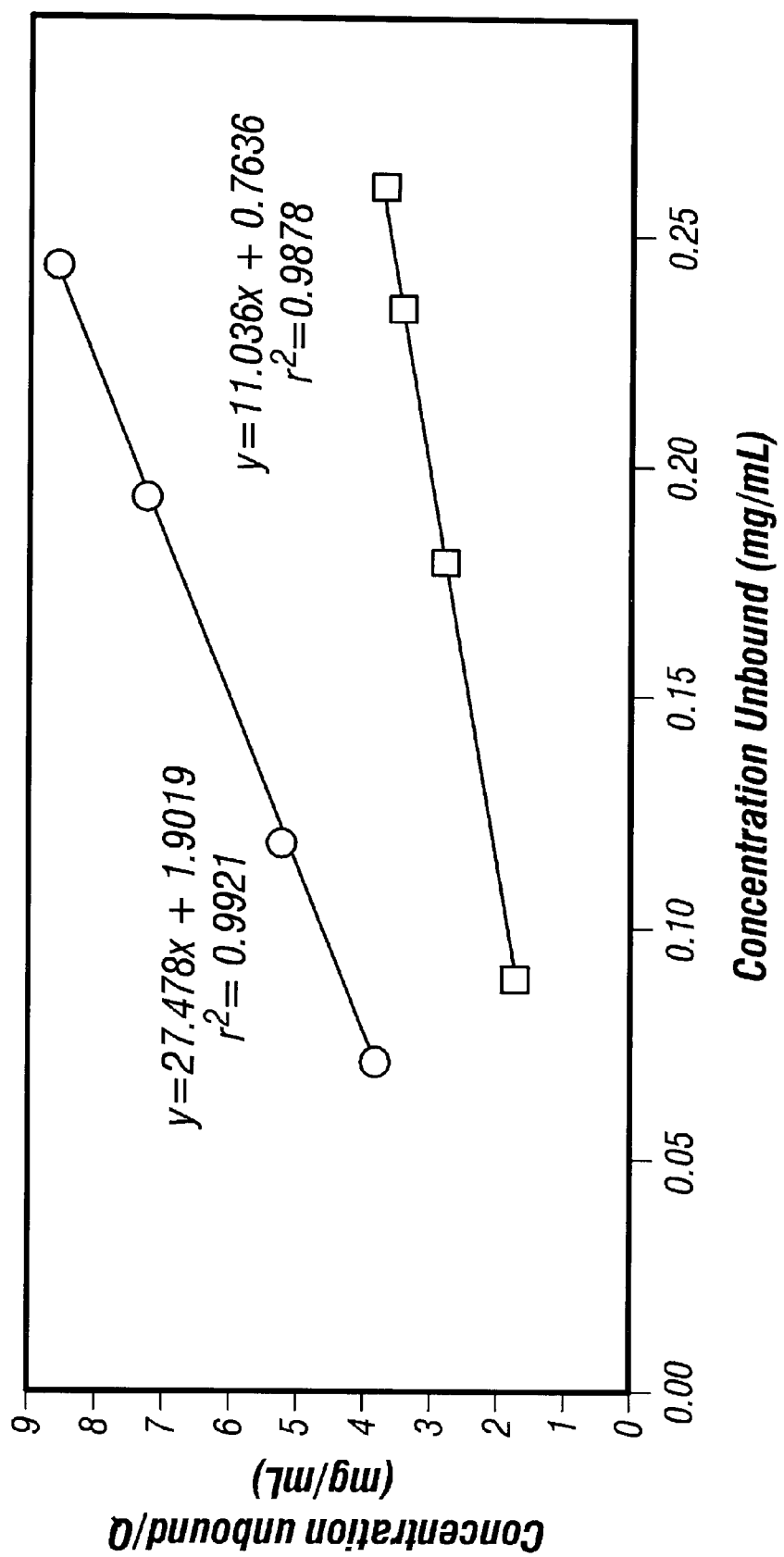
FIG. 6 is a graph showing Langmuir adsorption plots for PAC binding to (-○-) carrier particles with an iron:carbon ratio of 70:30 Type E carbon and (-□-) Type E carbon alone. Data were fit by simple unweighted linear regression.

Affinity ($K_m$) and maximal binding ($Q_m$) constants for PAC to the carrier particles having an iron:carbon ratio of 70:30 (Type E carbon) were determined over a range of carrier amounts. Table 4 below shows the results of adsorption isotherms of these compositions. The values were determined graphically from FIG. 6 and Langmuir's equation.

TABLE 4

| Adsorber | $K_m$ (L/mg) | $Q_m$ (mg/mg%) |
|---|---|---|
| Type E carbon alone | 0.014 | 9.1 |
| Carrier particles (70:30) with Type E carbon | 0.014 | 3.6 |

Affinity constant=($K_m$); and Maximum binding (mg drug/mg carrier)=($Q_m$)

PAC was loaded onto carrier particles and assayed by HPLC for drug content, and then allowed to release drug for 24 hours, or longer. Measurements and fluid replacement took place in 2 hour intervals up to 10 hours, and then daily thereafter. For the first 2 hours a magnetic field of 0.54 Tesla was applied to one set of two tubes containing the particles, while no magnetic field was applied to the controls set of tubes. No statistical difference was found in the PAC release profiles between carrier particles on which the drug was magnetically retained and those not subjected to a magnetic field (data not shown).

The PAC-adsorbed carrier particles and AC type E were pre-loaded using varying amounts of PAC. After 72 hours at 37° C. in porcine sera (4 mL), free PAC was extracted one time with 5 mL of ethyl acetate. The ethyl acetate extracts were individually taken to dryness in air, reconstituted in 5 mL of methanol, and filtered through Millex GV filters. Subsequent HPLC analysis indicated that cumulative drug release in 24 hrs and after 72 hrs averaged 67% for the carrier particles (range 53% to 86%) and averaged 64% for type E carbon. A low level of released PAC was subsequently validated independently by a bioassay system as described below.

C. Magnetic Field Capture of Carrier Particles in a Flowing Stream

A dynamic fluid flow circulation model similar to that described by Senyei et al. (*J. Appl. Phys.* 49(6):3578, 1978) was used to evaluate the forces and distances required to capture, retain, and accumulate carrier particles or iron in a flowing fluid at low (water) and high (35% glycerol) viscosities. The glycerol was used to simulate blood viscosity. Venous and arterial flow rates were simulated using flow rate and tubing diameter. Calibrated fluid flows were achieved with a precision syringe pump. The magnet was a neodymium-iron-boron magnet (2.4×3.5 cm). The magnetic field was measured using a gaussmeter at various distances from the magnet surface. The magnet was placed 5 cm above the effluent and moved in or out horizontally as needed to capture the iron or carrier particles. Complete (100%) capture, or retention, was the end-point of the experiment. Carrier particles or iron powder was introduced as a suspension through a syringe valve approximately 40 cm from the pump injection syringe and 40 cm from the effluent. In glycerol, the magnetic field necessary to retain 100% of iron or of the PAC-adsorbed particles was about 10% greater than in water.

A bioassay of tumor cytotoxicity from carrier particles loaded with PAC was carried out using a human squamous carcinoma cell line, SCC-9. Cell viability was independently determined following six days of incubation with each of: I) paclitaxel, 2) PAC-loaded carrier particles, 3) type E activated carbon, 4) free carrier particles, and 5) elemental iron. The assay was a slight variation of Mosmann's MTT cytotoxicity techniques. This spectrophotometric assay measures the quantitative reduction of the yellow tetrazolium salt of 3-[4,5-dimethylthiazol-2-yl]2,5-diphenyl-tetrazolium bromide] to its purple formazan derivative by the mitochondria of living cells. The amount of carrier used in these experiments was 0.5–117 g/mL. None of the controls, including DMSO (used for paclitaxel alone) were cytotoxic to the SCC-9 tumor cells.

A separate long-term CF clonogenic assay was evaluated concurrently. In this assay, cells were plated on 35 mm petri dishes and exposed to drug and controls as outlined above. Treated cells were incubated for 2–3 weeks to allow time for colonies to establish. These colonies were fixed in 2% acetic acid and 8% ethanol and stained with crystal violet. The colonies were counted under a Bella Glass Plate Reader. The $IC_{50}$ for the CF assay was $1\times10^{-2}$ g/mL for paclitaxel-adsorbed micro carriers, and $3\times10^{-3}$ g/mL for paclitaxel alone. The $IC_{50}$ by MTT assay for PAC released from carrier particles and paclitaxel alone were identical at both 500 and 1000 plated cells, $9\times10^{-3}$ g/well. The MTT assay for drug or chemically induced cytotoxicity is a surrogate marker for "true" cell kill. Therefore, usually more drug is required to demonstrate a given level of cell kill with the colony forming (CF) assay. Consequently, the dose response curve is shifted to a higher concentration level of paclitaxel.

Furthermore, no adverse effects were found from the magnetic field retention of drug-free carrier particles on the tumor cells in culture. The $IC_{50}$ for free paclitaxel alone was identical (5 ng/mL) to paclitaxel released from the carrier particles with or without magnet (5 ng/mL). In both instances the carrier particles showed no adverse effects on the cells during the in vitro cytotoxicity evaluation.

These results demonstrated that pharmacologically active paclitaxel can be released from the carrier particles of the invention, and that the chemical analysis of adsorbed and released drug can be confirmed biologically. Similar dose-response curves were obtained for free paclitaxel and paclitaxel desorbed from the carrier particles.

Iron:carbon carrier particles having various iron:carbon ratios in the range from 95:5 to 45:55 were prepared as described herein utilizing type A activated carbon as the carbon source. The particles were incubated in an adsorption solution containing 0.67 mg/ml of doxorubicin (Dox) in saline-citrate buffer (pH 7.4) to determine the capacity and binding of the Dox to composite particles of different composition. Table 5 below shows the results of these studies.

TABLE 5

| | Iron:Carbon ratio | | | | | | |
|---|---|---|---|---|---|---|---|
| | 95:5 | 85:15 | 75:25 | 65:35 | 60:40 | 55:45 | 45:55 |
| *Binding Capacity | 10.9% | 12.2% | 14.1% | 15.6% | 15.9% | 15.8% | 15.7% |
| ** % Binding | 69.0% | 78.7% | 89.4 | 99.5% | 100% | 100% | 99.7% |
| Tap Density (gm/cm$^3$) | 1.39 | 0.90 | 0.46 | 0.48 | 0.49 | 0.48 | 0.62 |
| Average Size ($\mu$) | 0.73 | 0.80 | 0.74 | 0.74 | 0.76 | 0.71 | 0.82 |

* Binding Capacity = mg Dox/mg carrier particles %
** % Binding = 4 mg Dox/25 mg carrier particles added The data in Table 5 shows the relationship between the iron:carbon content of the particles and drug binding to the particles.

EXAMPLE 6

Additional studies were conducted to compare the effect of the composition of the adsorption solution on the binding of the Dox to carrier particles having an iron:carbon ratio in the range 60:40 to 80:20. The following six test adsorption media compositions were formulated to provide sufficient viscosity to keep the carrier particles physically separate during adsorption of the Dox. The particles were first placed in the viscosity agent and the Dox/saline solution was later added.

1. 10% mannitol; 2% sodium carboxymethyl cellulose (CMC) (medium viscosity); 2% polyvinyl pyrrolidone (PVP in 50 mM citrate phosphate buffer
2. 5% mannitol; 2% CMC; 2% PVP in 50 mM citrate phosphate buffer.
3. 5% mannitol; 2% CMC; 2% PVP; 5% sorbitol in 50 mM citrate phosphate buffer.
4. 10% mannitol; 1% CMC; 2% PVP (K15) in 10 mM potassium phosphate buffer (pH 7.4).
5. 10% mannitol; 1% sodium CMC; potassium phosphate buffer (pH 7.4).
6. 5% sorbitol; 1% sodium CMC; 2% PVP (K1 5); 5% mannitol; in potassium phosphate buffer (pH 7.4)

Adsorption studies using each of the above adsorption media showed that the highest adsorption of Dox to the carrier particles was obtained using formulae 4, 5, and 6 of the above group.

Alternatively, the particles may be combined with the Dox/saline solution first and the viscosity agent added later.

In this process, 10% mannitol and 5% CMC provided desirable results.

EXAMPLE 7

Certain porphyrins are photosensitizing compounds useful in photodynamic therapy against tumors. The so called "second generation" photosensitizers possess major adsorption peaks at wavelengths 656 nm and many of these compounds are in clinical trials in the U.S., Japan, and Europe. Several classes of photosensitizers were screened for comparative binding to iron:carbon particles of various composition. The wavelength near the activation wavelength (often the $\lambda_{max}$) of a particular photosensitizer was used for quantitative drug measurements. It was found that concentrations of various porphyrins at 80 mcg/ml (0.11 mM) in phosphate buffered saline (PBS) pH 7.4 were convenient for initial binding studies. The photosensitizers tested were hematoporphyrin derivative (HPD); benzoporphyrin derivative monoacid A (BPD-ma); Photofrin® porfimer sodium (PF2); and clorin e6. For the binding studies, 10 mg of carbon or 50 mg of iron:carbon particles were optimum. An octanol/buffer (pH 7.4) partition coefficient for the four compounds was as follows: HPD=1; chlorin e6=1.1; PF2=0.1$\geq$; and BPD-ma=4000>.

The results of the binding studies are summarized in Table 6 below

TABLE 6

| iron:carbon ratio | HPD % binding mg/mg % | % | Clorin e6 % binding mg/mg % | % | PF2 % binding mg/mg % | % | BPD-ma % binding mg/mg % | % |
|---|---|---|---|---|---|---|---|---|
| 30:70 Type E | 0.4 | 37.0 | 0.7 | 68.8 | 0.08 | 7.2 | 0.25 | 23.0 |
| 30:70 Type A | 0.5 | 41.9 | 0.8 | 69.9 | 0.13 | 11.4 | 0.33 | 30.1 |

In order to achieve higher loading levels of BPD-ma, the binding capacity and fractional binding of the drug to four prototype iron:carbon carrier particles (MTCs, or, magnetic targeted compounds) was tested using 1.4 mM drug in isopropanol (with 0.5% 0.02 M acetic acid) as the adsorption medium and a longer equilibration period of 18 hours. As shown in Table 7 below, by this technique, a 30-fold increase in binding capacity from a 10-fold increase in the initial concentration of the drug was obtained.

TABLE 7

SUMMARY OF BINDING AND RELEASE OF BPD-ma

| | Carbon Type | | | |
|---|---|---|---|---|
| | A MTC26.2 | A MTC15.1 | E MTC5241 | E MTC5273 |
| iron:carbon ratio | 70:30 | 60:40 | 70:30 | 60:40 |
| Binding capacity (mg/mg %) | 9.5 | 13.9 | 11.0 | 11.7 |
| fractional binding % | 43.5 | 63.5 | 53.6 | 57.7 |
| % release (mg/mg bound) | 54.7 | 13.7 | 9.1 | 7.9 |

These studies showed that the carrier particles using Type A carbon in a 60:40 iron:carbon ratio (MTC 15.1) were significantly different than the other particles tested with respect to binding capacity and fractional binding of the total amount of the drug used. When a magnetic field was used facilitate washing each of the carriers free from unbound BPD-ma, the MTC 15.1 carrier particles did not give a clear solution as others did. It was assumed that a significant amount of carbon was released from the surface of the particles in the process of binding. By contrast, the carrier particles using TypeA carbon in a 70:30 iron:carbon ratio (MTC 26.2) gave up bound BPD-ma more efficiently than the other carriers tested while retaining a good level of initial adsorption.

EXAMPLE 8

In one sterilization technique, particles may be rendered sterile in a glass vial using gamma irradiation. In this system, at least 1000 vials may be sterilized at a time, using 2.5 to 3.5 Mrad's of gamma irradiation from a cobalt source. For instance, both particle lots 0198 (made with carbon A) and 0498 (made with carbon KB) were rendered sterile in this fashion. Each was tested after sterilization and found to have retained all manufactured properties, such as particle size distribution and doxorubicin binding capacity. Similarly, the aqueous solution of excipients may be rendered sterile through autoclave treatment at 121° C. for thirty minutes. For example, lot 0398 (100 mL/vial) and lot 0598 (20 mL / vial) were sterilized in this fashion. Each was tested after sterilization and found to have retained all manufactured properties, such as ability to suspend particles in a vehicle suitable for human administration.

EXAMPLE 9

Camptothecin has been shown to bind to MTC particles prepared with K carbon in a weight ratio of 75:25 Fe:C. Camptothecin may be bound to particles out of 0.9% saline solution or 10% lactose solution, but is preferentially bound from saline. The following graph shows binding across a range of solution concentrations, and indicate a maximum binding capacity of approximately 110 $\mu$g/mg MTC (11%) from saline.

TABLE 8

Camptothecin adsorption from Saline

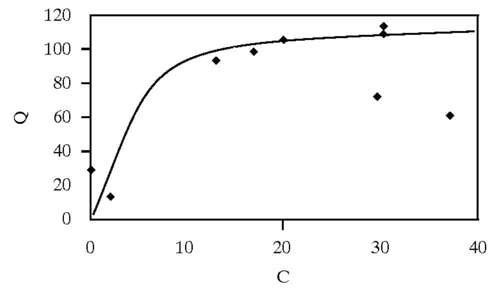

Camptothecin has two commercial derivatives, topotecan and irinotecan, and a third chemical derivative in clinical trials called aminocamptothecin. These derivatives represent minor chemical changes to the camptothecin molecule. These and other chemical derivatives should also bind.

EXAMPLE 10

Methotrexate has been shown to bind to MTC particles prepared with K carbon in a weight ratio of 75:25 Fe:C. Methotrexate may be bound to particles out of 0.9% saline solution or 10% lactose solution, but is preferentially bound from saline. The following graph shows binding across a range of solution concentrations, and indicate a maximum binding capacity of approximately 100 $\mu$g/mg MTC (10%) from saline.

TABLE 9

Methotrexate adsorption from saline

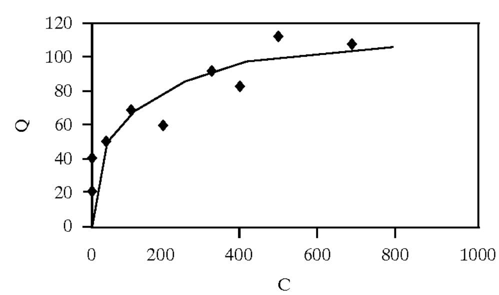

Methotrexate has one chemical derivative, aminopterin. This derivative represents a minor chemical change to the methotrexate molecule. These and other chemical derivatives should also bind. Methotrexate belongs to a class of molecules called folate antagonists. These molecules interfere with the synthesis of folate in a cancer cell. Folate antagonists are structurally similar, as their mode of action requires that they bind and inhibit the action of a specific enzyme. Examples of other folate antagonists are pyritrexin; 10-ethyl, 10-deaza-aminopterin; trimetrexate; 5,10-deaza, 10-proparglyfolic acid; and 5,10-dideazatetrahydrofolate. These and other folate antagonists should also bind.

EXAMPLE 11

Paclitaxel has been shown to bind to MTC particles prepared with K carbon in a weight ratio of 75:25 Fe:C.

Paclitaxel may be bound to particles out of ethanol or cremaphor EL formulation, but is preferentially bound from a citrate buffered aqueous ethanol mixture. The following graph shows binding across a range of solution concentrations, and indicate a maximum binding capacity of approximately 160 µg/mg MTC (16%) from citrated buffered aqueous ethanol. The binding extends to all concentrations between 0% and 16%.

TABLE 10

Langmuir Isotherm
Darco KB

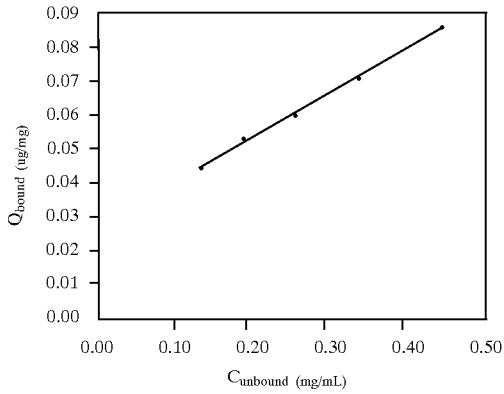

Paclitaxel has been bound to particles composed of three other carbons. The maximum binding observed in each is shown in the following table:

TABLE 11

| Carbon type | Maximum binding (µg/mg) |
|---|---|
| A | 190 |
| B | 174 |
| E | 82 |
| KB | 160 |

Paclitaxel is a chemical derivative of taxol, which has another chemical derivative, taxotere. There are other taxol derivatives, most semi-synthetic, that have similar structures to taxol and paclitaxel. These derivatives represents minor chemical changes to the taxol molecule. These and other chemical derivatives should also bind.

EXAMPLE 12

Verapamil has been shown to bind to MTC particles prepared with K carbon in a weight ratio of 75:25 Fe:C. Verapamil may be bound to particles out of lactose or saline solution, but is preferentially bound from an aqueous saline solution. The following graph shows binding across a range of solution concentrations, and indicate a maximum binding capacity of approximately 140 µg/mg MTC (14%) from saline. The binding extends to all concentrations between 0% and 14%.

TABLE 12

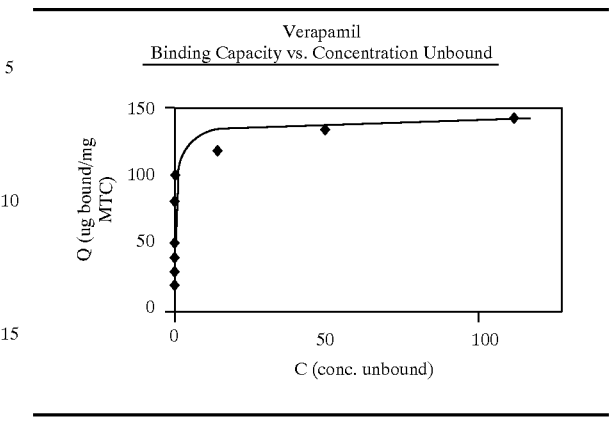

EXAMPLE 13

Ferrocarbon particles were prepared and doxorubicin was adsorbed for a resulting dose solution of 0.4 mg/ml doxorubicin and 5.0 mg/ml carrier. Selective catheterization of the hepatic artery was performed for delivery to Yorkshire domestic swine. Animals received 3–6 pulsed infusions every 10–30 minutes for a cumulative dose of 14.2–18 mg doxorubicin. An external magnet was held in position during the infusion procedure and for 15–30 minutes directly thereafter. Animals were evaluated over 28 days and then sacrificed. Histopathological evaluation showed that 18 mg doxorubicin given in 7.5 mL infusion cycles every 15 minutes was the maximum tolerated dose. This determination was based primarily on the occurrence of hepatic necrosis and portal area changes.

What is claimed is:

1. A magnetically responsive composition comprising particles including carbon and iron, wherein the carbon is substantially uniformly distributed throughout the particle volume, wherein the cross-sectional size of each particle is less than about 5 µm, and wherein the carbon is selected from the group consisting of types A, B, E, K, KB, and chemically modified versions thereof.

2. The composition of claims, wherein the particles are about 0.1 µm to 5.0 µm in cross-sectional size, each particle including a weight ratio of iron to carbon in the range from about 95:5 to 50:50, and having a therapeutic amount of doxorubicin. adsorbed thereon.

3. The composition of claim 2, wherein the weight ratio of iron to carbon is from about 80:20 to 60:40.

4. The composition of claim 3, wherein the average amount of doxorubicin is up to 20% of the mass of the particle.

5. The composition of claim 1, wherein the particles are about 0.1 µm to 5.0 µm in cross-sectional size, each particle including a weight ratio of iron to carbon in the range from about 95:5 to 50:50, and having a therapeutic amount of camptothecin, or an analog thereof, adsorbed thereon.

6. The composition of claim 5, wherein the weight ratio of iron to carbon is from 80:20 to 60:40.

7. The composition of claim 6, wherein the average amount of camptothecin is up to 20% of the mass of the particle.

8. The composition of claim 5, wherein the analog of camptothecin is topotecan.

9. The composition of claim 8, wherein the weight ratio of iron to carbon is from 80:20 to 60:40.

10. The composition of claim 9, wherein the average amount of topotecan is up to 20% of the mass of the particle.

11. The composition of claim 5, wherein the analog of camptothecin is irinotecan.

12. The composition of claim 11, wherein the weight ratio of iron to carbon is from 80:20 to 60:40.

13. The composition of claim 12, wherein the average amount of irinotecan is up to 20% of the mass of the particle.

14. The composition of claim 5, wherein the analog of camptothecin is aminocamptothecin.

15. The composition of claim 14, wherein the weight ratio of iron to carbon is from 80:20 to 60:40.

16. The composition of claim 15, wherein the average amount of aminocamptothecin is up to 20% of the mass of the particle.

17. The composition of claim 1, wherein the particles are about 0.1 μm to 5.0 μm in cross-sectional size, each particle including a weight ratio of iron to carbon in the range from about 95:5 to 50:50, and having a therapeutic amount of taxol, or an analog thereof, adsorbed thereon.

18. The composition of claim 17, wherein the taxol analog is taxotere.

19. The composition of claim 18, wherein the weight ratio of iron to carbon is from 80:20 to 60:40.

20. The composition of claim 19, wherein the average amount of taxotere is up to 20% of the mass of the particle.

21. The composition of claim 17, wherein the taxol analog is paclitaxel.

22. The composition of claim 21, wherein the weight ratio of iron to carbon is from 80:20 to 60:40.

23. The composition of claim 22, wherein the average amount of paclitaxel is up to 20% of the mass of the particle.

24. The composition of claim 1, wherein the particles are about 0.1 μm to 5.0 μm in cross-sectional size, each particle including a weight ratio of iron to carbon in the range from about 95:5 to 50:50, and having a therapeutic amount of verapamil, or an analog thereof, adsorbed thereon.

25. The composition of claim 24, wherein the weight ratio of iron to carbon is from 80:20 to 60:40.

26. The composition of claim 25, wherein the average amount of verapamil is up to 20% of the mass of the particle.

27. The composition of claim 1, wherein the particles are about 0.1 μm to 5.0 μm in cross-sectional size, each particle including a weight ratio of iron to carbon in the range from about 95:5 to 50:50, and having a therapeutic amount of a folate antagonist adsorbed thereon.

28. The composition of claim 27, wherein the folate antagonist is methotrexate.

29. The composition of claim 28, wherein the weight ratio of iron to carbon is from 80:20 to 60:40.

30. The composition of claim 29, wherein the average amount of methotrexate is up to 20% of the mass of the particle.

31. The composition of claim 27, wherein the folate antagonist is aminopterin.

32. The composition of claim 31, wherein the weight ratio of iron to carbon is from 80:20 to 60:40.

33. The composition of claim 32, wherein the average amount of aminopterin is up to 20% of the mass of the particle.

34. The composition of claim 27, wherein the folate antagonist is pyritrexin.

35. The composition of claim 34, wherein the weight ratio of iron to carbon is from 80:20 to 60:40.

36. The composition of claim 35, wherein the average amount of pyritrexin is up to 20% of the mass of the particle.

37. The composition of claim 27, wherein the folate antagonist is 10-ethyl, 10-deazaaminopterin.

38. The composition of claim 37, wherein the weight ratio of iron to carbon is from 80:20 to 60:40.

39. The composition of claim 38, wherein the average amount of 10-ethyl, 10-deazaaminopterin is up to 20% of the mass of the particle.

40. The composition of claim 27, wherein the folate antagonist is trimetrexate.

41. The composition of claim 40, wherein the weight ratio of iron to carbon is from 80:20 to 60:40.

42. The composition of claim 41, wherein the average amount of trimetrexate is up to 20% of the mass of the particle.

43. The composition of claim 27, wherein the folate antagonist is 5,10-deaza, 10-proparglyfolic acid.

44. The composition of claim 43, wherein the weight ratio of iron to carbon is from 80:20 to 60:40.

45. The composition of claim 44, wherein the average amount of 5,10-deaza, 10-proparglyfolic acid is up to 20% of the mass of the particle.

46. The composition of claim 27, wherein the folate antagonist is 5,10-dideazatetrahydrofolate.

47. The composition of claim 46, wherein the weight ratio of iron to carbon is from 80:20 to 60:40.

48. The composition of claim 47, wherein the average amount of 5,10-dideazatetrahydrofolate is up to 20% of the mass of the particle.

49. The composition of claim 1, wherein the particles are about 0.1 μm to 5.0 μm in cross-sectional size, each particle including a weight ratio of iron to carbon in the range from about 95:5 to 50:50, and having a therapeutic amount of a radioisotope adsorbed thereon.

50. The composition of claim 49, wherein the amount of radioisotope is from about 10 pgm to 700 ng.

51. The composition of claim 1, wherein the particles are about 0.1 μm to 5.0 μm in cross-sectional size, each particle including a weight ratio of iron to carbon in the range from about 95:5 to 50:50, and having a diagnostic amount of a radioisotope adsorbed thereon.

52. The composition of claim 51, wherein the amount of radioisotope is from about 10 pgm to 700 ng.

53. The composition of claim 1, wherein the particles are about 0.1 μm to 5.0 μm in cross-sectional size, each particle including a weight ratio of iron to carbon in the range from about 95:5 to 50:50, and having a therapeutic amount of a biologically active substance adsorbed thereon.

54. The composition of claim 53, wherein the biologically active substance is a drug, a radioactive substance, or genetic material.

55. The composition of claim 54, wherein the radioactive substance is $^{186}$Re, $^{188}$Re, $^{123}$I, $^{125}$I, or $^{90}$Y.

56. The composition of claim 1, wherein the particles are about 0.1 μm to 5.0 μm in cross-sectional size, each particle including a weight ratio of iron to carbon in the range from about 95:5 to 50:50, and having a diagnostic amount of a biologically active substance adsorbed thereon.

57. The composition of claim 56, wherein the biologically active substance is a radioisotope, a contrast agent, a dye or genetic material.

58. The composition of claim 57, wherein the radioactive substance is $^{186}$Re, $^{188}$Re, or $^{99}$Tc.

59. A magnetically responsive composition comprising particles made by a process of mechanically mixing carbon and iron powders, and wherein the carbon is substantially uniformly distributed throughout the particle volume.

60. The composition of claim 59, wherein the carbon is selected from the group consisting of types A, B, E, K, KB, and chemically modified versions thereof.

61. The composition of claim 59, wherein the particles have a further active substance adsorbed thereon.

62. The composition of claim 59, wherein the particles are suspended in a pharmaceutically acceptable excipient.

63. A composition for use in the manufacture of a magnetically responsive injectable preparation comprising a particles comprising iron and carbon, wherein the carbon is substantially distributed throughout the volume of the particle.

64. The composition of claim 63, wherein said preparation is dry.

65. The composition of claim 64, wherein said composition comprises one or more dry excipients.

66. The composition of claim 64, wherein said composition comprises one or more excipients in aqueous solution.

67. The composition of claim 63, wherein said preparation has been sterilized by gamma irradiation.

68. A method for local regional therapy comprising:
  a) intra-arterial injection of a magnetically responsive composition comprising particles comprising iron and carbon, wherein the carbon is substantially uniformly distributed throughout the particle volume, and at least one biologically active substance; and
  b) establishment of an external magnetic field adjacent to the therapy region.

69. The method of claim 68, wherein the magnetically responsive composition is delivered to a human breast.

70. The method of claim 68, wherein the composition is used as an embolic agent.

71. The method of claim 68, wherein said local regional therapy is treatment of at least one solid tumor, wherein said biologically active substance is at least one anti-tumor agent, and wherein said region is a tumor.

72. A method for increasing the concentration of a biologically active substance at an in vivo site comprising injecting into a patient a ferrocarbon particle produced by a joint deformation process resulting in the carbon being substantially uniformly distributed throughout the particle volume, and having said biologically active substance adsorbed thereon, and establishing an external magnetic field adjacent to the in vivo site where the increased concentration of the biologically active substance is desired.

73. The method of claim 72, wherein said in vivo site is a tumor.

74. The method of claim 72, wherein said biologically active substance is at least one anti-tumor agent.

* * * * *

UNITED STATES PATENT AND TRADEMARK OFFICE
CERTIFICATE OF CORRECTION

PATENT NO. : 6,482,436 B1
DATED : November 19, 2002
INVENTOR(S) : Volkonsky et al.

It is certified that error appears in the above-identified patent and that said Letters Patent is hereby corrected as shown below:

Column 24,
Line 44, please delete "of claims" and insert therefore, -- of claim 1 --.

Signed and Sealed this

Sixth Day of January, 2004

JAMES E. ROGAN
*Director of the United States Patent and Trademark Office*